US012690925B2

(12) United States Patent
Wendling et al.

(10) Patent No.: US 12,690,925 B2
(45) Date of Patent: Jul. 28, 2026

(54) METHOD AND SYSTEM FOR TRACKING AND VISUALIZING MEDICAL DEVICES

(71) Applicant: St. Jude Medical, Cardiology Division, Inc., St. Paul, MN (US)

(72) Inventors: Anthony Wendling, Watertown, MN (US); Fermin Armando Lupotti, Lake Forest, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 698 days.

(21) Appl. No.: 18/148,243

(22) Filed: Dec. 29, 2022

(65) Prior Publication Data

US 2023/0263580 A1     Aug. 24, 2023

Related U.S. Application Data

(60) Provisional application No. 63/312,869, filed on Feb. 23, 2022.

(51) Int. Cl.
*A61B 34/20* (2016.01)
*A61B 34/00* (2016.01)

(52) U.S. Cl.
CPC .............. *A61B 34/20* (2016.02); *A61B 34/25* (2016.02); *A61B 2034/2051* (2016.02); *A61B 2034/2055* (2016.02); *A61B 2034/254* (2016.02)

(58) Field of Classification Search
None
See application file for complete search history.

(56) References Cited

U.S. PATENT DOCUMENTS

| | | | |
|---|---|---|---|
| 5,697,377 A | 12/1997 | Wittkampf | |
| 5,983,126 A | 11/1999 | Wittkampf | |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |

(Continued)

FOREIGN PATENT DOCUMENTS

WO     2016/093848 A1     6/2016

OTHER PUBLICATIONS

Enriquez et al., "Use of Intracardiac Echocardiography in Interventional Cardiology", Circulation, May 22, 2018, vol. 137, pp. 2278-2294.

*Primary Examiner* — Angela M Hoffa
(74) *Attorney, Agent, or Firm* — Wiley Rein LLP

(57) ABSTRACT

An electroanatomical mapping system tracks and visualizes an item of interest, such as a medical device or anatomical structure, as the item moves within a non-ionizing localization field. The system localizes the item within the localization field and determines the initial position of the item with respect to an imaging device (e.g., an intracardiac echocardiography catheter) field of view. The system displays a region of the field of view containing the initial position of the item if it is within the field of view. If not, the system can output a notification. As the item moves, the system can update the displayed region so that it remains focused on the item, and can output a notification if the item exits the field of view. The displayed region(s) can include one or more two-dimensional image slices, optionally output as a three-dimensional volumetric image.

11 Claims, 5 Drawing Sheets

(56)     References Cited

U.S. PATENT DOCUMENTS

| | | | | |
|---|---|---|---|---|
| 6,990,370 | B1 | 1/2006 | Beatty et al. | |
| 8,041,413 | B2 * | 10/2011 | Barbagli | A61B 8/0833 |
| | | | | 600/459 |
| 8,285,364 | B2 * | 10/2012 | Barbagli | A61B 5/06 |
| | | | | 600/459 |
| 2006/0241445 | A1 | 10/2006 | Altmann et al. | |
| 2007/0167821 | A1 * | 7/2007 | Lee | A61B 8/12 |
| | | | | 600/463 |
| 2007/0167823 | A1 * | 7/2007 | Lee | A61B 8/12 |
| | | | | 600/463 |
| 2008/0119727 | A1 * | 5/2008 | Barbagli | A61B 90/36 |
| | | | | 600/437 |
| 2012/0035481 | A1 * | 2/2012 | Barbagli | A61B 90/36 |
| | | | | 600/443 |
| 2023/0039065 | A1 | 2/2023 | Dascal et al. | |

* cited by examiner

METHOD AND SYSTEM FOR TRACKING AND VISUALIZING MEDICAL DEVICES

CROSS-REFERENCE TO RELATED APPLICATIONS

This application claims the benefit of U.S. provisional application No. 63/312,869, filed 23 Feb. 2022, which is hereby incorporated by reference as though fully set forth herein.

BACKGROUND

The present disclosure relates generally to medical procedures, such as cardiac diagnostic and therapeutic procedures, including electrophysiological mapping and cardiac ablation. In particular, the present disclosure relates to the tracking and visualizing medical devices, such as electrophysiology mapping and ablation catheters, during such procedures via ultrasound imaging techniques.

Catheters are used for an ever-growing number of procedures. To name just a few examples, catheters are used for various electrophysiology procedures, including diagnostic, therapeutic, and ablative procedures. Typically, the catheter is manipulated through the patient's vasculature and/or body organs to the intended site, for example, within the patient's heart.

It is often desirable to provide a practitioner with a visualization (that is, an image) of the catheter within the heart. Although such images can be provided using ionizing radiation, it is also known to visualize the site of interest with ultrasound. In many such applications, an ultrasound transducer is mounted in a catheter that, analogous to the foregoing description of an electrophysiology catheter, can be navigated through a patient's vasculature and/or body organs to the site of interest.

One application of ultrasound imaging is intracardiac echocardiography (ICE). ICE techniques can be used to generate a three-dimensional volumetric image of a patient's heart or other anatomy from a plurality of two-dimensional ultrasound images taken from within the patient's heart. Advantageously, the ICE imaging modality can provide high-resolution real-time visualization of cardiac structures and continuous monitoring of catheter location within the heart, and can also aid in early recognition of potential complications.

It should be understood, however, that, in any given position and orientation, an ICE catheter can only image a certain volume (referred to herein as the "field of view" of the ICE catheter). Thus, if the medical device (e.g., electrophysiology catheter), anatomical structure, or other object of interest moves outside the field of view of the ICE catheter, the practitioner must manipulate the ICE catheter until the object of interest is reacquired (that is, the practitioner must manipulate the ICE catheter until the field of view once again encompasses the object of interest).

BRIEF SUMMARY

The instant disclosure provides a method of tracking a medical device within a non-ionizing localization field using an electroanatomical mapping system, including the electroanatomical mapping system: localizing the medical device within the non-ionizing localization field; determining whether or not the medical device falls within a field of view of an intracardiac echocardiography catheter; and upon determining that the medical device falls within the field of view, displaying a region of the field of view containing the medical device. The method can also include the electroanatomical mapping system, upon determining that the medical device does not fall within the field of view, outputting a negative imaging notification.

In embodiments of the disclosure, the method further includes the electroanatomical mapping system localizing the intracardiac echocardiography catheter within the non-ionizing localization field.

The region of the field of view that is displayed can include a two-dimensional image slice or a plurality of adjacent two-dimensional slices, the latter of which can optionally be displayed as a volumetric image.

According to aspects of the disclosure, the method further includes the electroanatomical mapping system: determining that the medical device has moved to a new location within the field of view; and displaying an updated region of the field of view containing the new location of the medical device.

In still further aspects of the disclosure, the method includes the electroanatomical mapping system: determining that the medical device has moved to a new location outside of the field of view; and outputting a negative imaging notification.

Also disclosed herein is a method of visualizing an item of interest as the item of interest moves within a non-ionizing localization field, using an electroanatomical mapping system. The method includes the electroanatomical mapping system: localizing the item of interest at an initial location within the non-ionizing localization field; determining, from the initial location, an initial position of the item of interest within a field of view of an intracardiac echocardiography catheter; and displaying an initial region of the field of view containing the initial position of the item of interest.

The method further includes the electroanatomical mapping system: localizing the item of interest at a subsequent location within the non-ionizing localization field; determining, from the subsequent location, a subsequent position of the item of interest within the field of view of the intracardiac echocardiography catheter; and displaying a subsequent region of the field of view containing the subsequent position of the item of interest.

Still further, the method can include the electroanatomical mapping system: localizing the item of interest at a subsequent location within the non-ionizing localization field; determining, from the subsequent location, that the item of interest is outside the field of view of the intracardiac catheter; and outputting a negative imaging notification.

It is contemplated that the step of determining, from the initial location, the initial position of the item of interest within the field of view of the intracardiac echocardiography catheter can include the electroanatomical mapping system: localizing the intracardiac echocardiography catheter within the non-ionizing localization field; and determining, from the localization of the intracardiac echocardiography catheter and the initial location, the initial position of the item of interest.

The initial region that is displayed can include a two-dimensional image slice or a plurality of adjacent two-dimensional image slices, the latter of which can optionally be displayed as a volumetric image.

The item of interest may be a medical device, such as an electrophysiology catheter, or an anatomical feature, such as a pulmonary vein. In the case of an anatomical feature, the step of localizing the item of interest at the initial location within the non-ionizing localization field can include the electroanatomical mapping system receiving a user input identifying the item of interest through a graphical user interface.

The instant disclosure also provides an electroanatomical mapping system for tracking a medical device within a non-ionizing localization field. The system includes a tracking and visualization module configured to: localize the medical device within the non-ionizing localization field; determine whether or not the medical device falls within a field of view of an intracardiac echocardiography catheter; and display a region of the field of view containing the medical device upon determining that the medical device falls within the field of view. The tracking and visualization module can further be configured to output a negative imaging notification upon determining that the medical device does not fall within the field of view.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for tracking and visualizing medical devices, as may be desirable during an electrophysiology study. For purposes of illustration, aspects of the disclosure will be described with reference to tracking and visualizing an ablation catheter, such as the FlexAbility™ Ablation Catheter, Sensor Enabled™ from Abbott Laboratories (Abbott Park, Illinois), using an ICE catheter, such as Abbott Laboratories' ViewFlex™ Xtra ICE catheter. Further, exemplary embodiments will be described in the context of an electrophysiology procedure carried out using an electroanatomical mapping system, such as the EnSite Precision™ cardiac mapping system or the Ensite™ X EP System, both also from Abbott Laboratories. Those of ordinary skill in the art will understand, however, how to apply the teachings herein to good advantage in other contexts and/or with respect to other devices.

Figure 1:
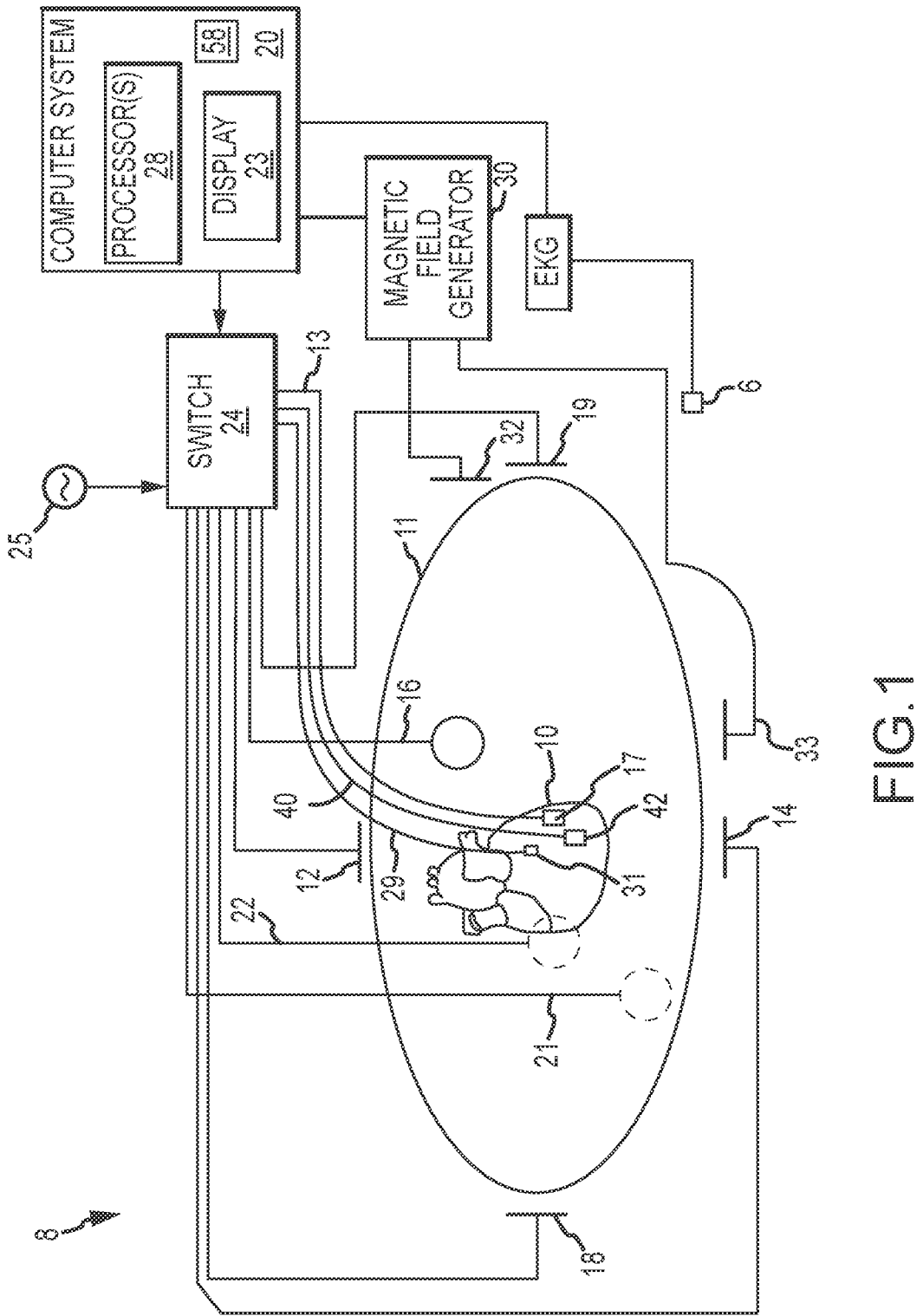
FIG. 1 is a schematic diagram of an exemplary electroanatomical mapping system.

FIG. 1 shows a schematic diagram of an exemplary electroanatomical mapping system 8 for conducting cardiac electrophysiology procedures, such as electrophysiological mapping and ablation. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference. This is referred to herein as "localization."

As depicted in FIG. 1 and described herein, system 8 can be a hybrid system that incorporates both impedance-based and magnetic field-based localization capabilities. In some embodiments, system 8 is the EnSite™ Velocity™ or EnSite Precision™ cardiac mapping system or the Ensite™ X EP System, all from Abbott Laboratories. Other electroanatomical mapping systems, however, may be used in connection with the present teachings, including, for example, the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario, Canada), and Stereotaxis, Inc.'s (St. Louis, Missouri) NIOBE® Magnetic Navigation System.

The localization and mapping systems described in the following patents (all of which are hereby incorporated by reference in their entireties) can also be used with the instant teachings: U.S. Pat. Nos. 6,990,370; 6,978,168; 6,947,785; 6,939,309; 6,728,562; 6,640,119; 5,983,126; and 5,697,377.

The foregoing systems, and the modalities they employ to localize a medical device, will be familiar to those of ordinary skill in the art. Insofar as the ordinarily-skilled artisan will appreciate the basic operation of such systems, therefore, they are only described herein to the extent necessary to understand the instant disclosure.

For simplicity of illustration, the patient 11 is depicted schematically as an oval. In the embodiment shown in FIG. 1, three sets of surface electrodes (e.g., patch electrodes) 12, 14, 16, 18, 19, and 22 are shown applied to a surface of the patient 11, pairwise defining three generally orthogonal axes, referred to herein as an x-axis (12, 14), a y-axis (18, 19), and a z-axis (16, 22). In other embodiments the electrodes could be positioned in other arrangements, for example multiple electrodes on a particular body surface. As a further alternative, the electrodes do not need to be on the body surface, but could be positioned internally to the body. Regardless of configuration, the patient's heart 10 lies within the electric field generated by patch electrodes 12, 14, 16, 18, 19, and 22.

FIG. 1 also depicts a magnetic source 30, which is coupled to magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings.

An additional surface reference electrode (e.g., a "belly patch") 21 provides a reference and/or ground electrode for the system 8. The belly patch electrode 21 may be an alternative to a fixed intra-cardiac electrode 31, described in further detail below. A magnetic patient reference sensor-anterior ("PRS-A") can also be positioned on the patient's chest to serve as a reference, analogous to surface reference electrode 21 and/or intracardiac reference electrode 31, for magnetic field-based localization modalities.

It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

Representative catheters 13, 40 are also shown schematically in FIG. 1. In aspects of the disclosure, catheter 13 can be an ablation catheter, such as the Abbott Laboratories FlexAbility™ Ablation Catheter, Sensor Enabled™, and catheter 40 can be an intracardiac echocardiography (ICE) catheter, such as the Abbott Laboratories ViewFlex™ Xtra ICE catheter. Catheters 13, 40 each respectively include one or more sensors 17, 42 for sensing the electric fields generated by patch electrodes 12, 14, 16, 18, 19, and 22 and/or the magnetic fields generated by magnetic field generators 32, 33.

In some embodiments, an optional fixed reference electrode 31 (e.g., attached to a wall of the heart 10) is shown on yet another catheter 29. Often, reference electrode 31 is placed in the coronary sinus and defines the origin of a coordinate system with reference to which catheters 13, 40 can be localized by system 8.

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Amongst other things, computer system 8 can interpret measurements by sensors 17, 42 of the magnetic and/or electrical fields generated by magnetic field generators 32, 33 and patch electrodes 12, 14, 16, 18, 19, and 22, respectively, to determine the position and orientation of catheters 13, 40 within heart 10. The term "localization" is used herein to describe the determination of the position and orientation of an object, such as catheter 13, within such fields.

Ultrasound imaging catheter 40 can be used to generate a three-dimensional volumetric image of heart 11 (or other anatomic structure) from a plurality of two-dimensional images using any of several techniques, including those disclosed in United States patent application publication no. 2006/0241445 (which is hereby incorporated by reference as though fully set forth herein) and international application publication no. WO 2021/150421, that will be familiar to those of ordinary skill in the art. Ultrasound imaging catheter 40 can also be used to generate a four-dimensional volumetric image of heart 11 (or other anatomic structure) using any of several techniques that will likewise be familiar to those of ordinary skill in the art.

In certain embodiments of the disclosure, field of view 44 of ultrasound imaging catheter 40 (depicted in FIG. 2) is about 90 degrees by about 90 degrees by about 12 cm, though these dimensions are merely exemplary, and it is contemplated that the size of field of view 44 can vary without departing from the scope of the instant disclosure.

Figure 2:
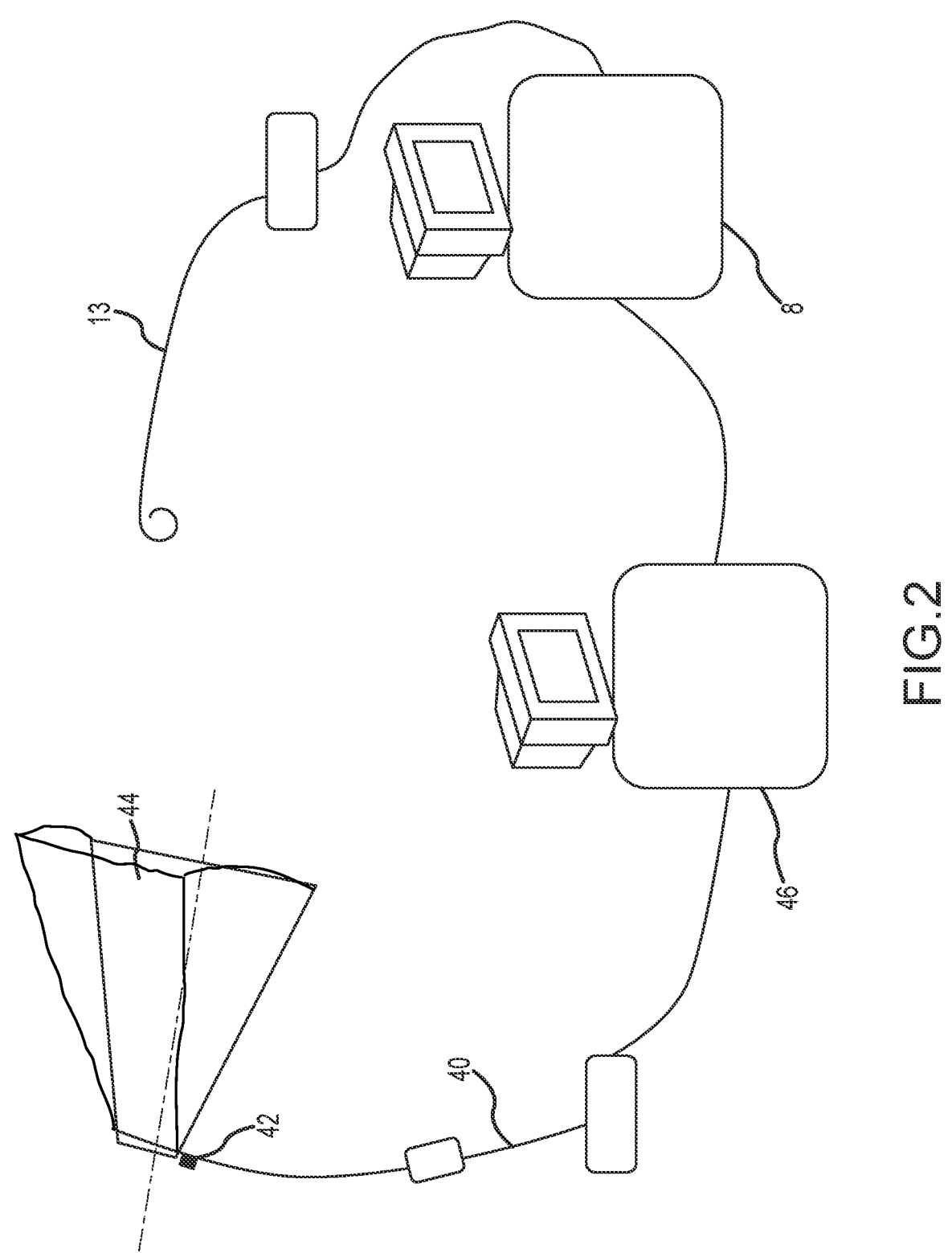
FIG. 2 is a schematic diagram of an embodiment of the instant disclosure illustrating the interconnections between an ultrasound imaging device, an electrophysiology catheter, an electroanatomical mapping system, and an ultrasound console.

Those of ordinary skill in the art will appreciate that various echographic imaging modalities, such as B-mode ultrasound and color Doppler echocardiography, may be employed to acquire the two-dimensional image slices that are then assembled into the three-dimensional volumetric image. In other aspects of the disclosure, a three-dimensional volumetric image of heart 11 (or other anatomic structure) can be generated by sampling the target volume with multiple ultrasound beams. In this regard in general, ultrasound imaging catheter 40 may be coupled to an ultrasound console 46, such as Abbott Laboratories' ViewMate™ Ultrasound Console, which may in turn be coupled to system 8 as shown in FIG. 2.

The foregoing discussion of ICE imaging is general, insofar as numerous aspects of ICE imaging, including the use of ICE imaging in connection with electrophysiology procedures, are well-understood by those of ordinary skill in the art and need not be described in detail herein. See, e.g., Enriquez et al., "Use of Intracardiac Echocardiography in Interventional Cardiology," Circulation, Vol. 137, Issue 21, pp. 2278-2294 (May 22, 2018). Thus, ICE imaging will only be described herein to the extent necessary to understand the instant disclosure.

Aspects of the disclosure relate to tracking and visualizing (e.g., on display 23 and/or ultrasound console 46) catheter 13 as it moves relative to the field of view of ultrasound imaging catheter 40. System 8 can therefore include a tracking and visualization module 58. According to some embodiments of the disclosure, tracking and visualization module 58 operates to automatically track and visualize catheter 13 as it moves relative to the field of view of ultrasound imaging catheter 40.

Figure 3:
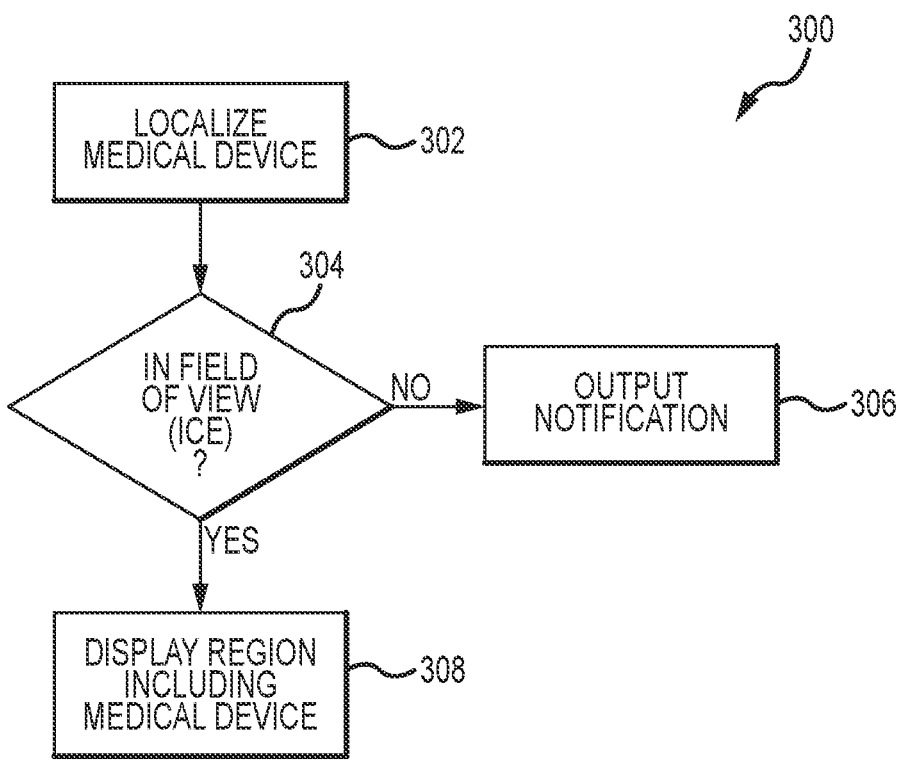
FIG. 3 is a flowchart of representative steps that can be carried out according to aspects of the instant disclosure.

One exemplary method according to aspects of the instant disclosure will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or tracking and visualization module 58). It should be understood that the representative steps described below can be either hardware- or software-implemented. For the sake of explanation, the term "signal processor" is used herein to describe both hardware- and software-based implementations of the teachings herein.

In block 302, system 8 localizes catheter 13 within the electrical and/or magnetic fields generated by patch electrodes 12, 14, 16, 18, 19, and 22 and/or magnetic field generators 32, 33. Localization of catheter 13 is described above and will also be familiar to those of ordinary skill in the art.

In decision block 304, system 8 uses the localization of catheter 13 to determine whether catheter 13 is inside or outside field of view 44 of ICE catheter 40. For instance, in certain embodiments of the disclosure, system 8 can localize ICE catheter 40 within the electrical and/or magnetic fields generated by patch electrodes 12, 14, 16, 18, 19, and 22 and/or magnetic field generators 32, 33, again as described above. The localization of ICE catheter 40, in turn, allows system 8 to determine the extent of field of view 44 relative to the coordinate system of system 8 (referred to herein as the "coordinate envelope" of field of view 44). This, in turn, allows system 8 to determine whether the localization of catheter 13 is inside or outside field of view 44 (e.g., if the localization coordinates of catheter 13 are within the coordinate envelope of field of view 44, then catheter 13 is inside field of view 44; otherwise, it is outside field of view 44).

Upon determining that catheter 13 is outside field of view 44 (the "NO" exit from decision block 304), system 8 can output a notification that catheter 13 is not within field of view 44 (block 306). This notification is referred to herein as a "negative imaging notification" and can be audible (e.g., sounded as an alarm), tactile (e.g., a vibration output in the handle of catheter 13), visual (e.g., shown on display 23), or any other suitable notification or combination of notifications to a practitioner.

If desired, the practitioner can adjust the position and/or orientation of ICE catheter 40 until field of view 44 includes catheter 13. It is also contemplated that, in certain embodiments of the disclosure, system 8 can provide cues to the practitioner to aid in such adjustments (e.g., provide an indication on display 23 directing the practitioner to rotate and/or deflect ICE catheter 40 a certain amount in a certain direction).

On the other hand, upon determining that catheter 13 is inside field of view 44 (the "YES" exit from decision block 304), system 8 can display (e.g., on display 23 and/or on ultrasound console 46) a region of field of view 44 including catheter 13. The displayed region can include a single two-dimensional image slice (e.g., the two-dimensional image slice that passes through the localization of catheter 13) or a plurality of adjacent two-dimensional image slices assembled into a three-dimensional volumetric image.

Figure 4A:
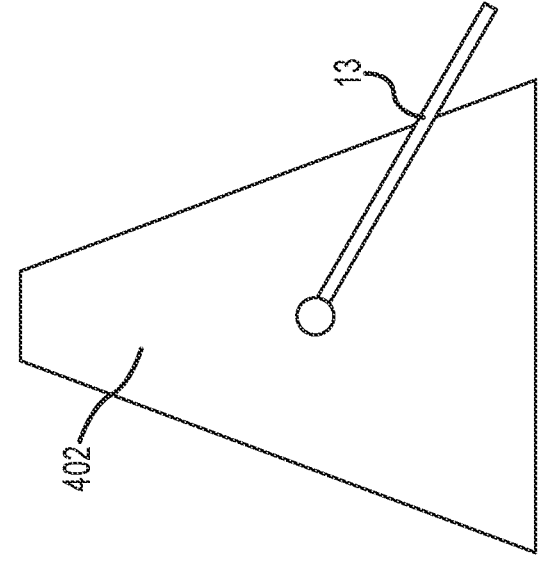
FIG. 4A illustrates tracking and visualizing a device according to embodiments disclosed herein with a two-dimensional image slice.
Figure 4A:
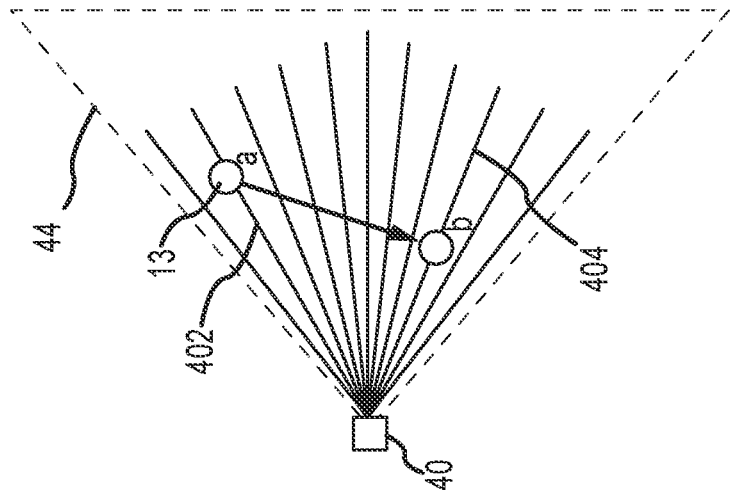

FIG. 4A schematically represents the display of a single two-dimensional image slice including catheter 13. As shown in FIG. 4A, catheter 13 is inside field of view 44 at location a, intersected by two-dimensional image slice 402. Thus, system 8 displays two-dimensional image slice 402.

Figure 4B:
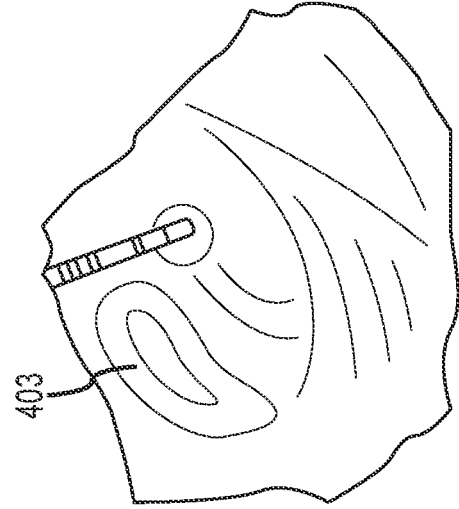
FIG. 4B illustrates tracking and visualizing a device according to embodiments disclosed herein with a three-dimensional volumetric image.
Figure 4B:
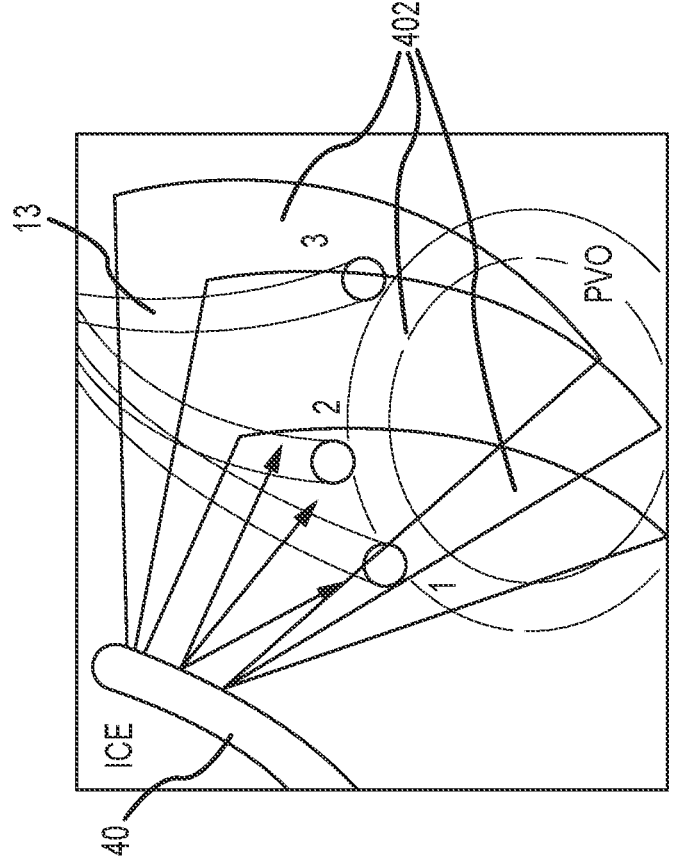

FIG. 4B illustrates the display of a plurality of two-dimensional image slices 402 as a three-dimensional volumetric image. As shown in FIG. 4B, each of the displayed image slices 402 intersects catheter 13. It is also contemplated, however, that additional two-dimensional slices that do not intersect catheter 13 may be displayed for context or reference (e.g., to show the position and orientation of catheter 13 relative to certain anatomical structures that may be of interest to the practitioner). The plurality of slices may, as shown in FIG. 4B, be displayed as a volumetric image 403.

The ordinarily-skilled artisan will appreciate that system 8 can monitor catheter 13 as it moves through the patient. Accordingly, in embodiments of the invention and consistent with the teachings above, system 8 can detect when catheter 13 has moved to a new location inside field of view 44 or has exited field of view 44.

In the latter case (e.g., catheter 13 has moved outside field of view 44), system 8 can output a negative imaging notification and, optionally, guide the practitioner to reposition and/or reorient ICE catheter 40 to reacquire catheter 13 within field of view 44.

In the former case (e.g., catheter 13 has moved, but remains inside field of view 44), system 8 can display an updated region of field of view 44 including the new location of catheter 13. As described above, the updated displayed region can include one or more two-dimensional image slices. Referring to FIG. 4A, for example, if catheter 13 moves from location "a" to location "b," system 8 can switch from displaying two-dimensional image slice 402 to displaying two-dimensional image slice 404.

Although several embodiments have been described above with a certain degree of particularity, those skilled in the art could make numerous alterations to the disclosed embodiments without departing from the spirit or scope of this invention.

For example, the teachings herein can not only be applied to track and visualize an electrophysiology catheter or other medical device within the field of view of an ICE catheter, but also to track and visualize other objects of interest, including anatomical structures, within the field of view of an ICE catheter. To the extent the object of interest is not directly localizable by system 8 (e.g., it is an anatomical structure, and therefore does not include electrodes, magnetic coils, or other sensors usable for localization), it can be identified by the practitioner through a graphical user interface (e.g., on display 23). For instance, the practitioner can use a mouse or other input device to "click" on an anatomical structure of interest (e.g., a pulmonary vein ostium) in order to select it for tracking, and system 8 can use image recognition algorithms to track the "clicked" (that is, selected) structure as it moves (e.g., as the heart beats and/or as the patient breathes).

As another example, the teachings herein can also be applied to track a medical device within the field of view of a transesophageal echocardiogram (TEE) probe carrying a sensor (e.g., 17, 42) to facilitate localization of the TEE probe.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of tracking a medical device within a non-ionizing localization field using an electroanatomical mapping system, the method comprising the electroanatomical mapping system:

localizing the medical device within the non-ionizing localization field;

localizing an intracardiac echocardiography catheter within the non-ionizing localization field;

determining a coordinate envelope of a field of view of the intracardiac echocardiography catheter from the localization of the intracardiac echocardiography catheter;

making an initial determination whether or not the medical device falls within the coordinate envelope of the field of view of the intracardiac echocardiography catheter; and when the initial determination is that the medical device falls within the coordinate envelope of the field of view, displaying a region of the field of view containing the medical device.

2. The method according to claim 1, further comprising, when the initial determination is that the medical device does not fall within the coordinate envelope of the field of view, outputting a negative imaging notification.

3. The method according to claim 1, wherein the region of the field of view includes a two-dimensional image slice.

4. The method according to claim 3, wherein the region of the field of view includes a plurality of adjacent two-dimensional image slices.

5. The method according to claim 4, wherein the plurality of adjacent two-dimensional slices are displayed as a volumetric image.

6. The method according to claim 1, further comprising the electroanatomical mapping system:

determining that the medical device has moved to a new location within the field of view; and displaying an updated region of the field of view containing the new location of the medical device.

7. The method according to claim 1, further comprising the electroanatomical mapping system:

determining that the medical device has moved to a new location outside of the field of view; and outputting a negative imaging notification.

8. The method according to claim 1, wherein displaying the region of the field of view containing the medical device comprises initializing a display of the region of the field of view containing the medical device.

9. An electroanatomical mapping system for tracking a medical device within a non-ionizing localization field, the system comprising:

a display; and a processor configured to:

localize the medical device within the non-ionizing localization field;

localize an intracardiac echocardiography catheter within the non-ionizing localization field;

determine a coordinate envelope of a field of view of the intracardiac echocardiography catheter from the localization of the intracardiac echocardiography catheter;

make an initial determination whether or not the medical device falls within the coordinate envelope of the field of view of the intracardiac echocardiography catheter; and output to the display a region of the field of view containing the medical device when the initial determination is that the medical device falls within the coordinate envelope of the field of view.

10. The electroanatomical mapping system according to claim 9, wherein the processor is further configured to output a negative imaging notification upon making a subsequent determination that the medical device does not fall within the field of view.

11. The electroanatomical mapping system according to claim 9, wherein the output comprises an initialized region of the field of view containing the medical device.

\* \* \* \* \*